(12) United States Patent
McIntyre et al.

(10) Patent No.: US 6,278,079 B1
(45) Date of Patent: Aug. 21, 2001

(54) LASER CUTTING OF FABRIC GRAFTS

(75) Inventors: John P. McIntyre, Vista; Matthew R. Bye, Pacifica, both of CA (US)

(73) Assignee: Edwards Lifesciences Corp., Irvine, CA (US)

( * ) Notice: Subject to any disclaimer, the term of this patent is extended or adjusted under 35 U.S.C. 154(b) by 0 days.

(21) Appl. No.: 09/247,733

(22) Filed: Feb. 9, 1999

(51) Int. Cl.$^7$ .............................. B23K 26/08; B23K 26/00
(52) U.S. Cl. ................................ 219/121.67; 219/121.69; 623/116; 623/113
(58) Field of Search ................... 219/121.67, 121.69, 219/121.7, 121.71; 606/194, 195, 198; 623/1.16, 1.13, 1.31, 1.35

(56) References Cited

U.S. PATENT DOCUMENTS

| | | |
|---|---|---|
| 4,588,871 | 5/1986 | Etcheparre et al. . |
| 4,673,409 * | 6/1987 | Van Kampen . |
| 4,729,766 | 3/1988 | Bergentz et al. . |
| 5,200,592 | 4/1993 | Yabu . |
| 5,326,356 | 7/1994 | Della Valle et al. . |
| 5,614,115 | 3/1997 | Horton et al. . |
| 5,628,782 | 5/1997 | Myers et al. . |
| 5,782,904 | 7/1998 | White et al. . |
| 6,071,307 * | 6/2000 | Rhee et al. . |

* cited by examiner

Primary Examiner—Clifford C. Shaw
Assistant Examiner—Jonathan Johnson
(74) Attorney, Agent, or Firm—Edwards Lifesciences, LLC; Guy L. Cumberbatch; Peter Jon Gluck

(57) ABSTRACT

A graft forming apparatus and method including a plurality of mandrels for receiving tubular grafts thereon and an adjacent cutting instrument for forming regular and repeated patterns of small holes therein and for severing the ends of the graft. The cutting instrument is preferably a low-powered laser to form clean and non-frayed holes and lines in fabric grafts. The mandrel are mounted for rotation about an axis underneath the cutting instrument which is movable along the axis. By computer control, the motion of the cutting instrument and mandrel can be accurately and precisely choreographed. The mandrel may be a straight cylinder for forming straight grafts, or may be a bifurcated mandrel formed of several components. The bifurcated mandrel includes a trunk portion and pair of detachable leg portions. Adapter disks are provided so that the bifurcated mandrel can be rotated either about the axis of the trunk portion, or about the axis of one of the leg portions. The holes are formed to precise dimensions and locations so that support wires may be weaved through the holes and circumferentially around the tubular graft to form a non-leaking supported tubular prosthesis.

7 Claims, 8 Drawing Sheets

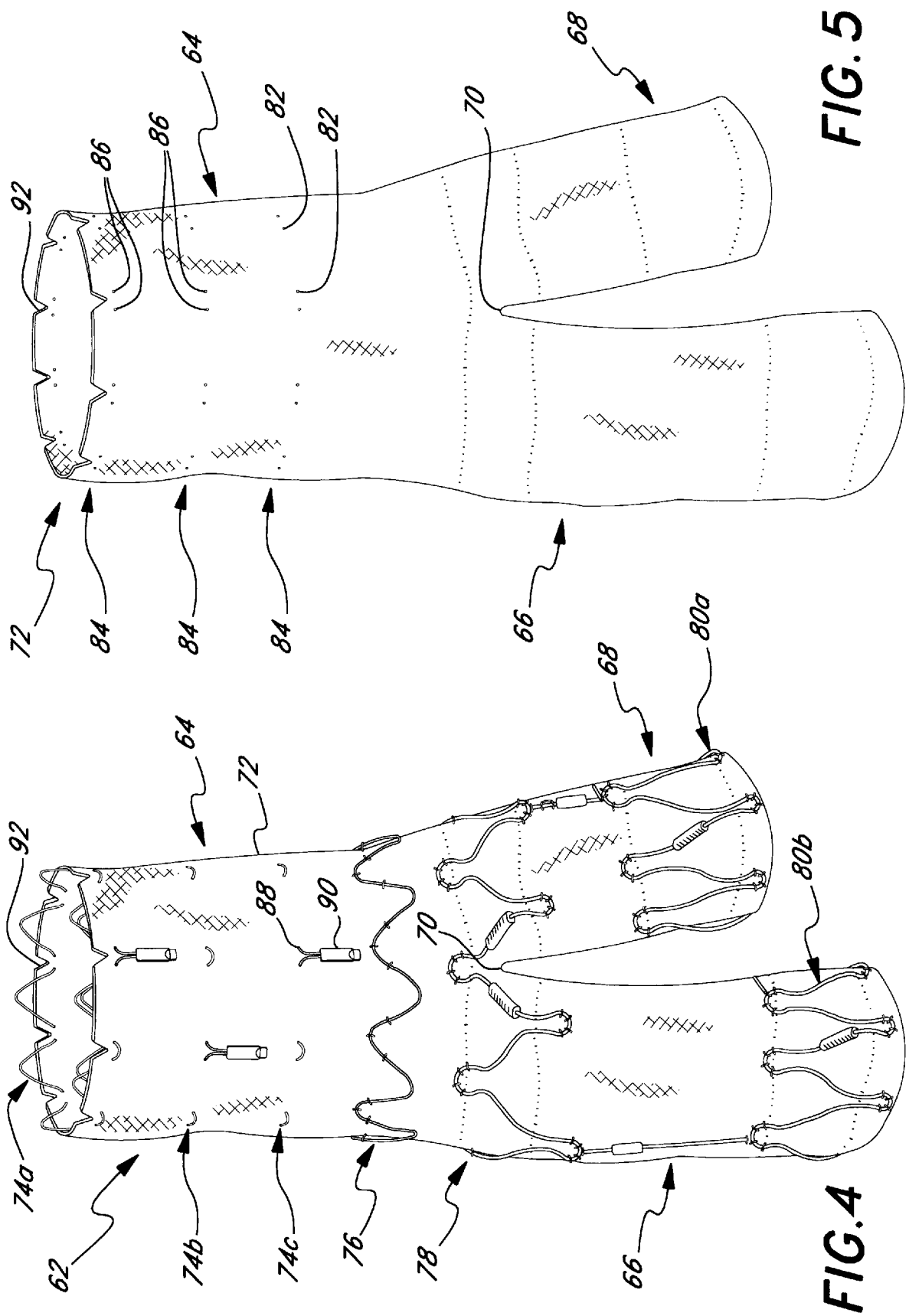

LASER CUTTING OF FABRIC GRAFTS

BACKGROUND OF THE INVENTION

1. The Field of the Invention

The present invention is related to methods and apparatus for forming a tubular prosthesis, and more specifically, to methods and apparatus for laser cutting a tubular fabric graft.

2. Description of the Related Art

Stents and vascular grafts of various designs are known for the treatment of aneurysms as well as for the treatment of occlusive diseases of the blood vessels or other ducts. A common type of tubular prosthesis includes a graft made of a biocompatible material having mechanical properties that can withstand varying internal pressures. The graft may be supported by an internal or external stent, or by a plurality of expandable circular wires. One such wire-supported intraluminal graft is disclosed in U.S. Pat. No. 5,782,904, issued Jul. 21, 1998.

Many grafts of the prior art, such as in the '904 patent, are made of porous textile material, usually a crimped or resiliently circular-knitted stocking of polymerized ethylene-glycol-terephthalate (Dacron™). Such textile grafts must often be treated blood, or "pre-clotted," before they are implanted to improve initial leak-resistance and biocompatibility. In recent years, vascular grafts have been made of expanded polytetrafluoroethylene (PTFE) possessing a porosity and flexibility such that no pre-treatment with blood is necessary.

In general, tubular grafts and their respective support and/or attachment means fall into two major categories, self-expanding and pressure expandable. Self-expanding intraluminal tubular prostheses include grafts supported and/or attached via resilient or shape-memory material such as spring steel or Nitinol™. Self-expanding material is capable of being formed in a configuration from which it may be compressed to a radially compact diameter for placement within a damaged vessel. At the time of use, the memory feature of these materials causes them to self-expand from the radially compact diameter to the expanded operative diameter.

Pressure-expandable tubular prostheses include grafts supported and/or attached via plastically deformable material such as stainless steel that is initially formed in its radially compact diameter. This type of material does not have memory, and will remain in the radially compact diameter until manually expanded. Typically, outwardly directed pressure is exerted upon the prosthesis through use of a balloon so as to cause radial expansion and resultant plastic deformation of the material to its operative diameter.

If individual circular wires are used as opposed to a cylindrical stent, consideration must be given to the attachment means between the wires and tubular graft such that uniform and durable support is provided. Some designs stitch the wires to the exterior of the tubular graft. This stitching may ultimately fail, however, and more importantly the support provided to the tube may be inadequate, especially when high negative pressures are present within the lumen of the tube. U.S. Pat. No. 5,782,904 describes the use of thin, stainless-steel undulating wires that are woven through the fabric of the tube such that spaced segments of each wire are outside the tube with the remainder of that wire inside the tube. In this manner, fairly even support is provided to withstand varying pressures in the lumen of the tube. One drawback, however, is the time-intensive nature of weaving a plurality of undulating wires in specific locations along the tube. The weave pattern must be laboriously pre-marked on the outside of the tube. The assembly process is made even more complex if the graft is branched, such as a bifurcated or so-called "trouser graft."

In the prior art processes for forming grafts, tubular lengths of fabric or PTFE material are cut to individual graft lengths using a heated cautery wire. Shears or other mechanical cutters are unsuitable for fabric grafts because the cut ends tend to fray. The use of a heated wire, however, creates difficulties such as fumes and excessive melting of the material, and is also fairly time-consuming and imprecise.

Lasers are often used for cutting textile material for garments and sailcloth, for example. Examples of the use of lasers in the textile industry can be seen in U.S. Pat. Nos. 4,588,871, 5,200,592, and 5,614,115. However, lasers have not been used for forming grafts, although they have been employed to perforate material for bioprosthetic applications. For instance, U.S. Pat. No. 5,326,356 discloses using a laser to render biocompatible material porous for use in skin grafts, and U.S. Pat. No. 4,729,766 discloses using a laser to form indentations in the exterior surface of an otherwise impermeable tube to encourage tissue ingrowth. In another example, U.S. Pat. No. 5,628,782 discloses the use of a laser to macroscopically perforate an outer tube for covering a fiber-wrapped vascular graft. In all these examples, the goal is to render an otherwise impermeable material porous.

Despite many advances in the field of tubular grafts, there remains a need for an improve method of forming such grafts, and in particular a need to shorten and automate the process for forming which will produce more uniform, and more efficacious, grafts.

SUMMARY OF THE INVENTION

The present invention provides a method of forming a tubular prosthesis including the steps of providing a tube of biocompatible material and fitting the tube on a rotatable mandrel. A laser is directed onto the tube, the laser having sufficient power to cut through the material without excessive melting or burning of the material. A graft portion of the prosthesis is formed from the tube, and a plurality of spaced holes are formed around the circumference of the graft. The graft is then removed from the mandrel, and at least one support wire is weaved through the spaced holes and around the circumference of the graft. In one embodiment, the material is a fabric and the laser is a low-powered, sealed, RF-excited laser operated so as to cut through the fabric material and fuse the cut ends without excessively melting or discoloring the material. In one embodiment, the laser is focused to have a nominal beam width of approximately 0.152 mm (0.006 inches), and the holes formed thereby are between 0.178 mm (0.007 inches) and 0.229 mm (0.009 inches). Preferably, the laser is a CO2 laser, and emits light energy in the infra-red spectrum.

The method may be used for straight grafts, or bifurcated grafts. If bifurcated grafts are being formed, the mandrel comprises a trunk portion and a pair of detachable leg portions. In a first step in the process, the trunk portion is rotated concentrically and the spaced holes are formed in the trunk portion of the graft. Subsequently, the mandrel is reconfigured so that one of the legs rotates concentrically, with the trunk portion rotating off-center, and one of the graft legs is cut to size. By repositioning the graft on the mandrel, the other of the graft legs is cut to size.

The present invention also provides a system for forming bioprosthetic trouser grafts, comprising a frame having a cutting instrument mounted for linear motion thereon. An elongated graft-supporting mandrel is provided including a trunk portion and a pair of removable leg portions. The system includes a rotatable chuck and associated secondary support spaced therefrom, both adapted to be fixed with respect to the frame. The chuck and secondary support are configured to rotate the mandrel therebetween about an axis parallel to and adjacent the linearly movable cutting instrument. The chuck and secondary support are preferably mounted for linear motion on a rail fixed with respect to the frame. The cutting instrument preferably comprises a low-powered, sealed, RF-excited laser positioned to direct a beam of light energy onto the generatrix of the mandrel facing the cutting instrument.

In another aspect, the present invention provides a mandrel kit for forming bifurcated grafts. The kit includes a generally cylindrical trunk portion having a first and a second end. A pair of leg portions removably attach to the second end of the mandrel to form a bifurcated mandrel for receiving an unfinished bifurcated graft. The kit may include a first adapter disk having a centered cylindrical cavity therein for receiving the first end of the trunk portion, the disk further including a centered shaft stub extending in the opposite direction from the centered cavity. A leg portion adapter having a pair of off-center holes for receiving the leg portions, and a centered shaft stub extending from the side opposite the pair of holes is also preferably provided. Additionally, the kit may include a second adapter disk having an off-center cylindrical cavity therein for receiving the first end of the trunk portion and a centered shaft stub extending in the opposite direction from the off-center cavity. Furthermore, a second leg portion adapter may be provided having a centered hole for receiving one of the leg portions, and a centered shaft stub extending from the side opposite the center hole.

BRIEF DESCRIPTION OF THE DRAWINGS

FIG. 4 is a front view of a bifurcated prosthesis manufactured in accordance with the present invention;

FIG. 5 is a front view of a graft portion of the prosthesis of FIG. 4;

FIG. 7a is an end view of a trunk portion of the mandrel assembly of FIG. 7;

DESCRIPTION OF THE PREFERRED EMBODIMENTS

Figure 1:
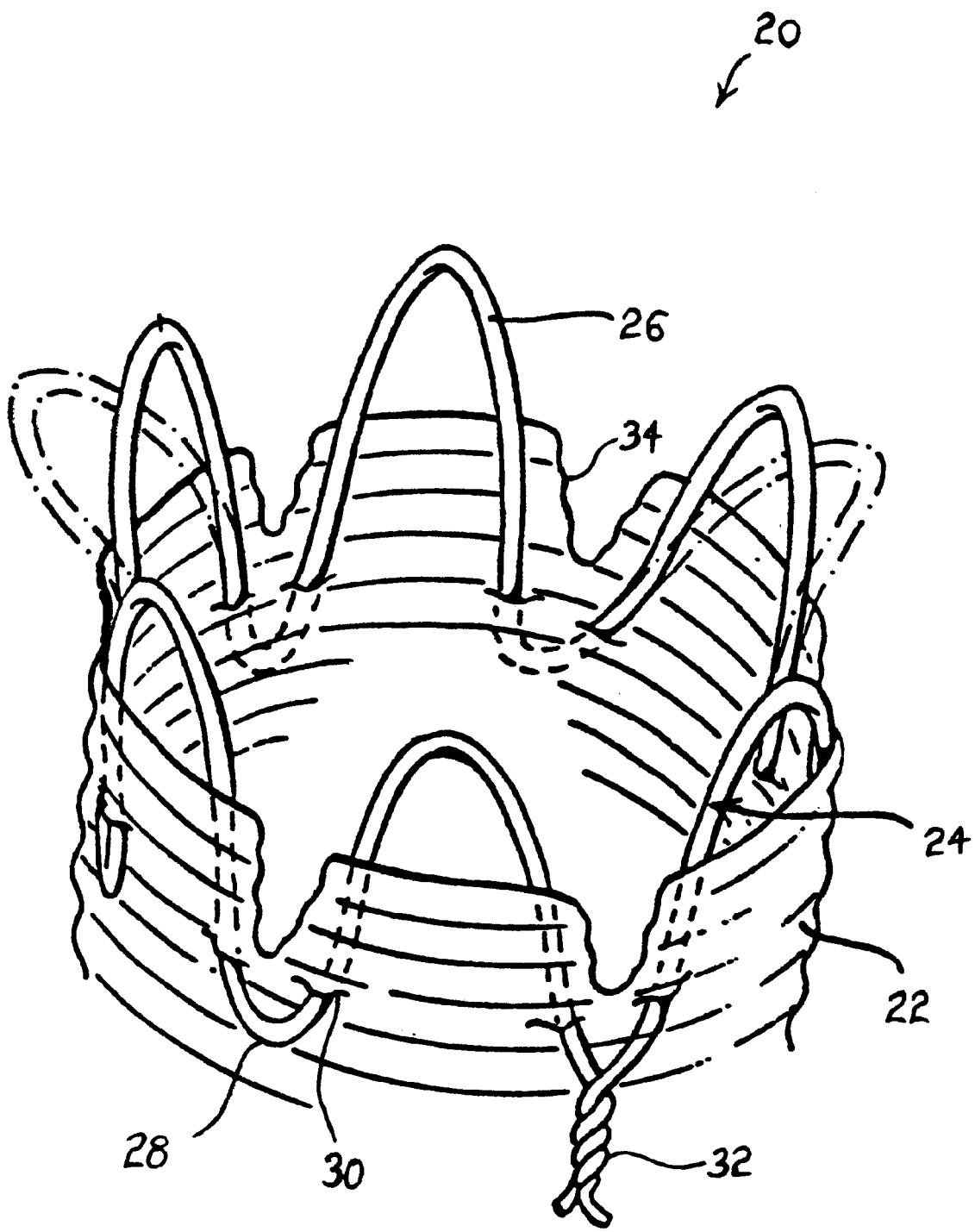
FIG. 1 is a detailed perspective view of one end of a wire-supported tubular prosthesis of the prior art.

FIG. 1 illustrates one end of prior art tubular prosthesis 20 having a crimped, fabric graft portion 22 and plurality of undulating support wires 24. The support wire 24 at the terminal end of the graft portion 22 includes crests 26 that project beyond the graft portion. In between crests 26, valleys 28 are forcibly woven through the material of the graft portion 22 thus defining apertures 30. In this respect, therefore, the valleys 28 are the only portions of wires exposed to the exterior of the graft portion 22, with the majority of each wire providing internal support thereto. The wires 24 are formed of the single strand, and are joined together at opposite ends by twisting, such as seen at 32. The twisted portion may be covered with some form of sleeve or collar, not shown.

As mentioned, the crests 26 of the wire 24 at the terminal end of the graft portion 22 project beyond the graft portion, and the mouth of the graft portion therebetween includes notches 34 to reduce the potential for the material flapping or otherwise creating flow disturbances in the lumen of the prosthesis 20. The notches 34 are typically formed after the wire 24 at each end is woven through the fabric of the graft portion 22, which is time-consuming.

Figure 2:
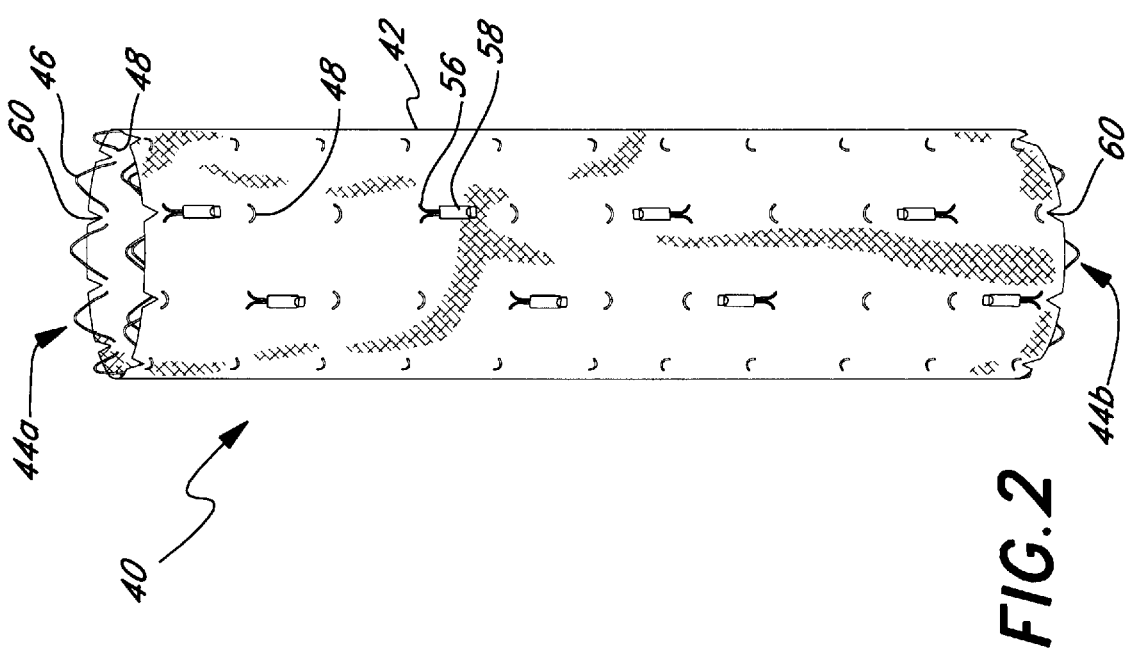
FIG. 2 is a front view of a straight tubular prosthesis manufactured in accordance with the present invention.

One embodiment of a vascular prosthesis formed in accordance with the present invention is seen at 40 in FIG. 2. The prosthesis 40 is a straight tube and may be utilized in a variety of clinical locations, one of which being an extension for a bifurcated prosthesis positioned in the abdominal artery to connect with the iliac arteries. These extension grafts typically comprise straight or tapered cylindrical tubes, with an upstream end having a common diameter, while the diameter of the downstream ends can vary depending on the anatomy of the patient. The upstream ends interlock with the respective downstream portions of the bifurcated prosthesis. By fixing the diameter of the upstream ends of the extension graft and the downstream ends of the bifurcated aortic graft, a consistent interface and interlock can be achieved regardless of the patient's anatomy. The diameter of the downstream end of the graft extensions can be provided in varying diameters so as to suit the diameter of the iliac artery into which graft portions are being implanted. The change in diameter can be provided by a short step-down portion or a step-up portion or by a region of taper extending along a length of the graft portion. It will be appreciated that the graft forming techniques described herein may be adapted for straight, tapered, or other shaped grafts.

With reference to FIG. 2, the straight tubular prosthesis 40 includes a flexible tubular structure 42 that is reinforced by wireforms 44 extending circumferentially therearound. The flexible tubular structure 42 is foldable and the wireforms are radially compressible and expandable. Thus, the prosthesis 40 is configured to move between an insertion diameter, in which state the graft may be inserted through a femoral and iliac artery and into one of the bifurcated legs of the aortic graft, and a larger, expanded diameter (illustrated in FIG. 2).

The flexible tubular structure 42 is preferably made of a tube of woven polyester fabric, preferably polymerized ethylene-glycol-terephthalate (Dacron™). Although polyester is presently preferred, other materials may be utilized for the flexible tubular structure 42. Such materials include but are not limited to expanded polytetrafluoroethylene (ePTFE), coated polyester, porous polyurethane, silicone, and spun or woven polymeric fibers. One of skill in the art of biocompatible grafts will readily identify other materials suitable for application in the construction of the flexible tubular structure 42. It is preferred that the tubular structure be made of a material which is porous, thereby allowing tissue ingrowth into the graft material and/or formation of an intimal layer, although for some applications it may be desirable to make the tubular structure of a fluid impervious material.

If a fabric is used, it is preferably woven into the tubular configuration, thereby eliminating seams or other internal protrusions that could interfere with blood flow or form locations for thrombi to occur. By employing a flexible fabric for the tubular structure, the fabric will readily fold to accommodate radial contraction of the graft, such as is necessary for intraluminal introduction of the graft.

In accordance with a presently preferred embodiment of the invention, a number of balloon-expandable wireforms 44 are provided to furnish structural rigidity to the graft and to secure the graft within the body lumen. Each of the balloon-expandable wireforms is similarly configured with an undulating geometry such as a closed sinusoidal-like wave, with alternating crests 46 and valleys 48. Alternatively, the balloon-expandable wireforms are configured such that they are continuously curvilinear. An alternative method for constructing the balloon-expandable wireforms is to configure the wireforms in a true sinusoidal pattern. One of skill in the art will be familiar with other methods for manufacturing balloon-expandable wireforms without departing from the teachings of the present invention. In one particular embodiment, the crests 46 and valleys 48 are formed with a radius which of about 0.025 inches. Additionally, the amplitude of each wireform is defined as the longitudinal distance between a crest 46 and an adjacent valley 48. In a preferred embodiment, the amplitude of the wireforms in their expanded states is approximately 2.61 mm (0.103 inches).

The balloon-expandable wireforms 44 of the present invention are preferably made of an alloy of carbon, silicon, phosphorus, sulphur, chromium, nickel, beryllium, cobalt, iron, manganese and molybdenum which is sold under the ELGILOY trade name by Elgiloy, L.P. of Elgin, Ill., U.S.A. Other materials that may be utilized in making the wireforms include a nickel -titanium shape memory alloy sold under the NITINOL trade name, stainless steel, and other biocompatible, implantable metals. The wires used in manufacturing the balloon-expandable wireforms of the present invention are preferably about 0.3 mm (0.012 inches) in diameter.

The balloon-expandable wireforms that are positioned along the graft extension are preferably secured to the tubular structure 42 by weaving the wireform through holes 50 (FIG. 3) formed in the tubular structure. The wire is woven through the tubular structure 42 such that the distal tip of the valley 48 of each wireform extends through the graft and is positioned on the outside of the fabric structure. The weaving is accomplished by initially configuring an elongated piece of wire into the predetermined curvilinear configuration. With the wire so configured, it may be manually woven through the holes 50 formed in the tubular structure 42 until the wire extends around the entire circumference of the tubular structure. The wire is woven such that it is primarily positioned along the interior of the tubular structure 42, with only small segments of wire exposed to the outside of the tube.

Figure 3A:
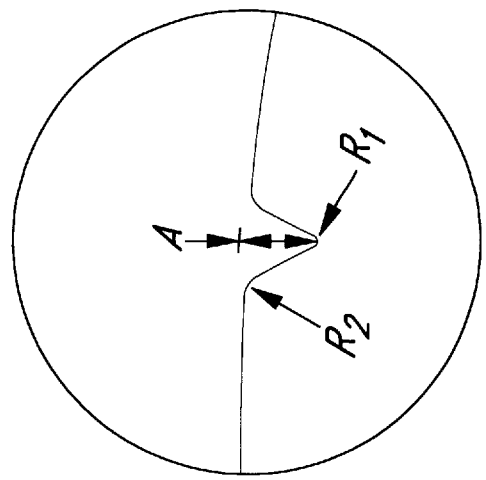
FIG. 3 is a front view of a graft portion of the prosthesis of FIG. 2.
Figure 3:
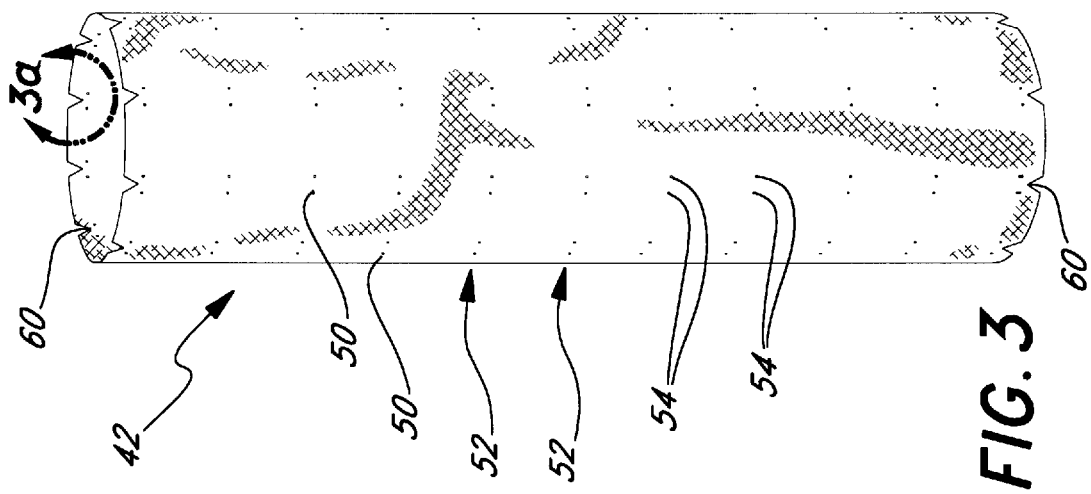

FIG. 3 illustrates just the flexible tubular structure 42 without the wireforms 44. The holes 50 can be seen in a plurality of axially spaced circumferential rows 52. Each row 52 includes a plurality of pairs 54 of holes 50, so that a portion of a wireform 44 may be threaded in and out at that location. More specifically, as seen in FIG. 2, each valley 48 is exposed to the exterior of the tubular structure 42 via a pair 54 of the holes 50.

The holes 50 are of a size and shape which prevents blood seepage between the edge of each hole and respective wireform 44. Specifically, the holes 50 are desirably circular and smaller in diameter than the diameter of the cylindrical wireforms 44 so as to form an interference fit. The tubular structure 42 is flexible and expands slightly when a larger wireform passes through one of the undersized holes 50. The holes 50 have a diameter of less than 95% with respect to the wireform diameter, preferably between about 8% and 92%, and more preferably between about 58% and 75%. Thus, if the wireform has a diameter of 0.3 mm (0.012 inches) the holes 50 desirably have a diameter of between about 0.025 mm (0.001 inches) and 0.279 mm (0.011 inches), and more preferably between about 0.178 mm (0.007 inches) and 0.229 mm (0.009 inches). The process for forming the holes 50 to be precisely circular, within proper size ranges, and located accurately will be described in greater detail below.

In a preferred embodiment, the pairs 54 of holes 50 are spaced apart with respect to one another with a tolerance of +0.254 mm (0.010 inches) and −0.0 mm. There are preferably six to twelve rows 52 with eight pairs 54 in each row. The total number of holes 50 may be between 100 and 200. Each hole 50 location has a tolerance of +0.254 mm (0.010 inches) and −0.254 mm (−0.010 inches).

As seen in FIG. 2, the wireform is woven into the tubular structure 42 such that when the wire extends around the entire periphery, and the free ends of the wire protrude from the tube at positions adjacent to each other defining a tail segment 56. The loose ends are preferably held together with a crimping sleeve 58. After crimping the sleeve to secure the ends to each other and thereby complete the circular configuration of the wireform, any portion of the wires extending beyond the ends of the sleeve may be trimmed to cleanly finish the tail segment.

The most proximal wireform 44a and the most distal wireform 44b are positioned with respect to the upper and lower edge of the tubular structure 42 such that approximately one-third of the wireform extends beyond the respective edge of the tubular structure. In particular, the proximal-most wireform is positioned to extend above the mouth of the tubular structure 42 to prevent any portion of the structure from oscillating, or "flapping," in response to the flow of blood past the edge of the graft.

As an additional measure to prevent such oscillation in the blood stream, the proximal and distal edges of the tubular structure 42 are configured with rounded V-shaped notches 60 corresponding generally to the valleys 48 of the proximal and distal wireforms, as seen in FIGS. 3 and 3a. Thus, the risk of the existence of any loose material that could potentially be affected by the passing flow of blood is substantially reduced. The notches are formed to precise dimensions including a depth A of about 0.686 mm (0.027 inches), a point radius $R_1$ of about 0.279 mm (0.011 inches) and a fillet radius $R_2$ of about 1.727 mm (0.068 inches).

Desirably, the wireforms are positioned adjacent one another and are spaced apart from each other such that the wireforms do not interfere with each other in either a radially expanded or contracted state. Thus, for example, the valleys of one wireform are located proximal of the crests of the next adjacent wireform. Preferably, the wireforms are also aligned "in phase," with peaks along one longitudinal line and adjacent valleys aligned along a second longitudinal line, thereby further reducing the possibility of overlap of adjacent wireforms. (While there may be some overlapping of the tail segments with an adjacent wireform, because the tail segments extend on the outside of the fabric layer and the adjacent wireform is primarily on the inside of the fabric layer, a small degree of overlap with an adjacent wireform does not pose a problem.) Another important feature of the straight prosthesis 40 of the present invention is the spacing distance between adjacent wireforms. It has been discovered in accordance with the investigations of the present invention that optimizing the spacing distance between the wireforms improves the balance between kink resistance and flexibility in the graft extensions. Too much space promotes kinking, while too little space detracts from flexibility. These are important features in the often tortuous path of the iliac arteries and abdominal aorta in which the graft extensions are to be placed. In this respect, accurate and precise location of the rows 52 of pairs 54 of holes 50 is essential to proper functioning of the prosthesis 40.

As illustrated in FIG. 4, another embodiment of tubular prosthesis fabricated by the techniques of the present invention is designated generally at 62. This bifurcated prosthesis, sometimes referred to as a "trouser graft," is adapted for insertion transfemorally to the situs of an aortic aneurysm in the region where the iliac arteries branch from the abdominal aorta.

The prosthesis 62 includes a trunk portion 64 that bifurcates into two legs 66, 68 at a septum region 70. The cylindrical tubes defined by the two legs 66, 68 are in fluid communication with the trunk portion 64, thereby approximating the internal configuration of the bifurcated junction of the aortic artery. In this preferred embodiment, one leg 66 extends longer than the other leg 68 to facilitate loading of both legs into a smaller diameter catheter-based loader when self expanding wireform is are attached to the end of each leg.

The bifurcated prosthesis 62 comprises a flexible tubular graft portion 72 (FIG. 5) reinforced by a variety of wireforms extending circumferentially around or woven into the structure. The graft portion 72 is foldable, and the wireforms are radially compressible and expandable. Thus, the graft is configured to move between an insertion diameter, in which state the graft may be inserted intraluminally into the aorta, and a larger, expanded diameter (illustrated in FIG. 4) in which state the graft may be secured within the aorta.

The bifurcated prosthesis 62 includes two different types of wireforms: balloon-expandable wireforms and self-expanding wireforms. This preferred embodiment includes three balloon expandable wireforms 74a, 74b, and 74c, which are woven into the trunk region 64 of the graft portion 72 but are positioned primarily on the interior thereof, and a single exterior balloon-expandable wireform 76 positioned at the distal end of the trunk region 64. A self-expanding wireform 78 is attached to the outside of the graft portion 72 at the septum region 70 with a self-expanding wireform 80a positioned on the distal end of the longer leg 66 and another self-expanding wireform 80b at the distal end of the shorter leg 68.

The balloon-expandable wireforms 74a, 74b, and 74c are preferably made of an alloy as more specifically described above, and preferably have a circular cross-section of about 0.3 mm (0.012 inches) in diameter. In addition, each of the balloon-expandable wireforms 74a, 74b, and 74c is similarly configured with a curvilinear geometry such as the closed sinusoidal-like wave illustrated in FIG. 2, with alternating crests and valleys.

The balloon-expandable wireforms 74a, 74b, and 74c that are positioned along the upper portion of the trunk 64 are preferably secured to the graft material by weaving through a plurality of holes 82. FIG. 5 illustrates just the tubular graft portion 72 bereft of wireforms. The holes 82 can be seen in a plurality of axially spaced circumferential rows 84. Each row 84 includes a plurality of pairs 86 of holes 82, so that a portion of each wireform 74 may be threaded in and out at that location. More specifically, as seen in FIG. 4, each valley is exposed to the exterior of the tubular graft portion 72 via a pair 86 of the holes 82.

As in the straight tube embodiment, each wireform 74 is woven into the graft portion 72 such that when the wire extends around the entire periphery of the fabric tube, the free ends of the wire protrude from the tube at positions adjacent to each other, thereby enabling a tail segment 88 to be defined by the free ends. The loose ends are preferably held together with a crimping sleeve 90 positioned over them.

The distal balloon-expandable wireform 76 is attached to the graft portion 72 in a different manner from the other balloon-expandable wireforms. Instead of being woven into the graft portion 72, distal wireform 76 is attached to the fabric by tying it to the fabric with polyester thread. Other biocompatible threads may also be employed for securing the distal wireform 76 to the graft portion 72. Although in this preferred embodiment, wireform 76 is tied to the fabric structure with a thread, one of skill in the art will readily identify other attachment methods, including threading through the graft portion 72.

The configuration of each of the self-expanding wireforms 78 and 80 is naturally biased towards an expanded state, such as that illustrated in FIG. 4. The self-expanding wireforms may be made of the same base material used in the construction of the balloon-expandable wireforms, although the method of manufacturing may differ. Thus, ELGILOY wire is preferred, with a number of other materials acceptable for such use. Attachment of the self-expanding wireforms 78 and 80 is preferably accomplished by tying the crests and valleys to the graft portion 72, as illustrated in FIG. 4. It is presently preferred that each crest and valley be tied in five separate locations around the perimeter of the loop defining the respective crest or valley.

In the expanded state illustrated in FIG. 4, the trunk portion 64 is generally cylindrical and has mouth 91 configured with rounded V-shaped notches 92 corresponding generally to the valleys of the terminal wireform 74a. Thus, the risk of the existence of any loose material that could potentially be affected by the passing flow of blood is substantially reduced.

The graft portion 72 is preferably made of a tube of woven polyester fabric, although other materials may be utilized as was described previously with respect to the graft portion 42 of FIG. 3.

System for Laser Forming Grafts

Figure 6:
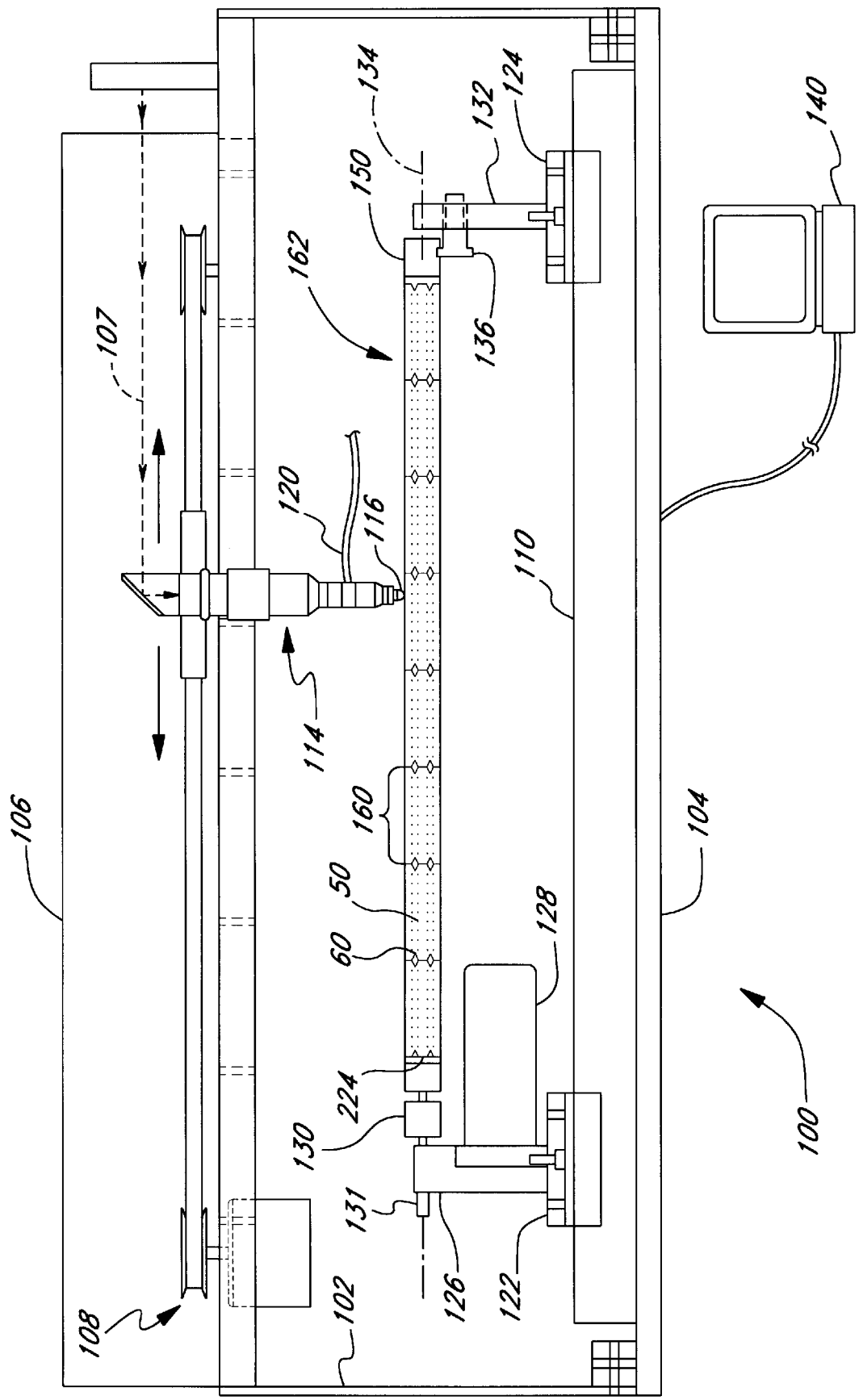
FIG. 6 is a schematic elevational view of a system for forming grafts in accordance with present invention.

A system 100 for forming grafts in accordance with the present invention is schematically shown in FIG. 6. The illustrated system 100 shows the basic components for forming grafts on a single mandrel, and it will be appreciated as explained below that multiple mandrels in a full-scale production version may be provided. In addition, the various components for providing motion and for cutting the grafts are exemplary only, and other means may be used.

The system 100 comprises a frame 102 mounted on base 104, the frame supporting a laser 106 and linear displacement mechanism 108 above a guide rail 110. The laser 106 generates a beam 107 of light energy which is directed at a series of mirrors and/or lenses (not shown) ultimately terminating at a movable mirror 112 forming a portion of a cutting instrument 114. The cutting instrument 114 comprises a vertically disposed, generally cylindrical member having one or more focusing lenses therein and an output lens 116 on its bottom end. The cutting instrument 114 is fastened to a toothed belt 118 which is driven horizontal left and right by the aforementioned linear displacement mechanism 108. A flexible hose 120 attaches to a lower end of the cutting instrument 114 and supplies a gas to an internal chamber communicating with outlet ports (not shown) on the bottom of the cutting instrument and surrounding the output lens 116.

The guide rail 110 supports a pair of carriages 122, 124 which slide thereon and can be fastened in different locations along the guide rail. Preferably, the guide rail 110 and carriages 122, 124 include respective elements of a precision linear bearing arrangement, such as a conventional tongue and groove linear slide. The left carriage 122 supports an upstanding frame 126 to which is mounted a servo motor 128. The output shaft of the servo motor 128 communicates with a drive arrangement (not shown) ultimately turning a chuck 130 rotatably coupled to the frame 126. The drive arrangement may include a belt drive and an encoder 131 is desirably provided to monitor the angular position of the chuck shaft to accommodate for any belt slip and ensure rotational accuracy. The chuck 130 extends horizontally from the frame 126 toward the right carriage 124 and an upstanding frame 132 mounted thereon. The chuck 130 rotates about an axis 134 and includes an internal jaw mechanism (not shown) for clamping to mandrels, as will be described below. The right end frame 132 includes bearings which support a pair of horizontally spaced wheels 136. The wheels 136 preferably include a pair of peripheral elastomeric rings and are spaced apart to be in position to support a cylinder of a predetermined diameter rotating about the axis 134. The axis 134 is in the same vertical plane as the output lens 116 of the cutting instrument 114. The cooperation between the support wheels 136 and chuck 130 will be described in greater detail below with respect to individual mandrels and graft forming techniques.

A computer control device 140 synchronizes the horizontal movement of the cutting instrument 114 and the rotating movement of the chuck 130. Various means are known for coordinating multiple moving elements in a manufacturing environment, and the present invention should not be construed as being limited to any one. One preferred embodiment of control system is a [programmable, multi-axis digital motion control system using DC servo motors coupled to optical rotary encoders. A 3 axis controller is required. Two axis are use for motion and the third is used to control the power of the laser. Custom software is written in the native language of the controller to control the path of the laser beam and to modulate the laser power to produce the drilled holes and cuts in the fabric. The software is written in such a way to take advantage of the symmetry of the holes and notches in the graft. For example, grafts of different diameters, having the same hole and notch patterns can be processed using the same program by changing only the number that designates the diameter of the graft in the program. A preferred controller is the DMC-1500 available from Galil Motion Control Inc. of Mountain View Calif. The chuck 130 is driven by a servo motor and directly coupled to a rotary encoder to insure precision in angular positioning of the chuck. Such precision is desirable when forming particular grafts, such as those shown in FIGS. 2–5. Of course, other graft forming applications such high precision may not be needed and a conventional belt drive or other similar expedient may be substituted.

Apparatus for Forming Straight Grafts

An elongated cylindrical mandrel 150 is shown extending between the chuck 130 and the support wheels 136. As the mandrel 150 rotates about the axis 134, an upper generatrix of the mandrel directly faces the output lens 116. In other words, the beam of light energy from the output lens 116 projects directly downward and impinges on the uppermost tangential surface of the cylindrical mandrel 150. The mandrel 158 includes a shaft stub 152 projecting from the left end that is captured by the jaws of the chuck 130. In this regard, the support wheels 136 (inclusive of the peripheral elastomeric rings) have outer diameters and are spaced apart so as to contact and support the mandrel 150 for rotation about the axis 134. Alternatively, a shaft stub may be provided on the right end of the mandrel 150 to rest on the wheels 136. The mandrel 150 preferably comprises stainless-steel, but may be made of other suitable materials.

FIG. 6 illustrates the graft forming system 100 in the process of forming a plurality of straight grafts 160 (such as the graft shown in FIG. 3) out of an elongated tube of fabric material 162. The various steps in forming the grafts 160 will be described in more detail below in the method of use section.

Apparatus for Forming Bifurcated Grafts

Figure 7:
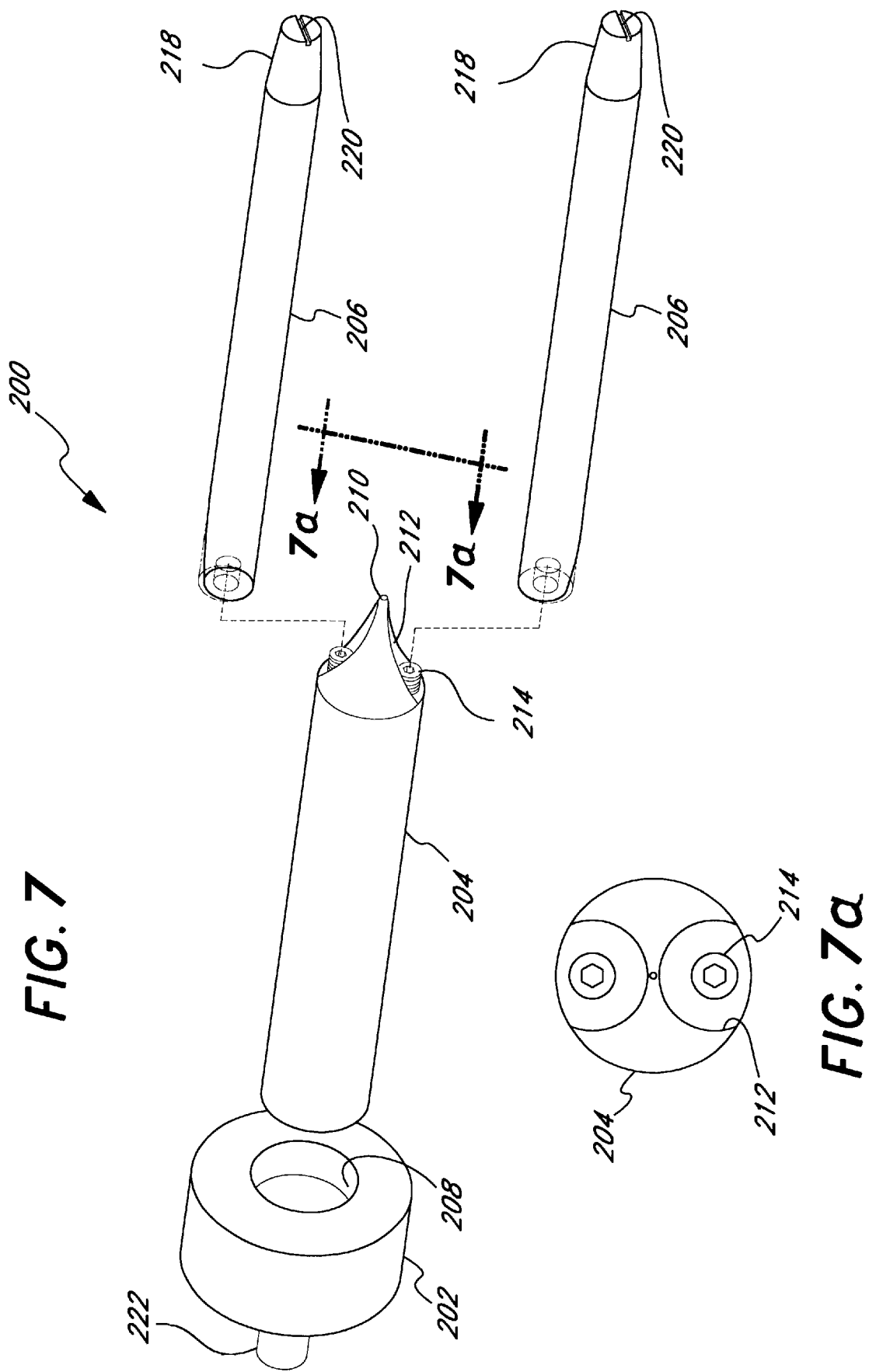
FIG. 7 is a perspective exploded view of a mandrel assembly for forming bifurcated grafts for use in the system of FIG. 6.

With reference to FIGS. 7 and 7a, a mandrel 200 used in forming bifurcated grafts, such as the graft shown in FIG. 5, is seen in exploded perspective view. The mandrel 200 comprises, from left to right, a first adapter disk 202, a generally cylindrical trunk portion 204, and a pair of identical legs 206. The first adapter disk 202 includes a central cylindrical cavity 208 sized to closely receive the left end of the trunk portion 204. The right end of the trunk portion 204 narrows in a cone shape to a tip 210. A pair of diametrically opposed and axially extending cylindrical reliefs 212 at the conical right end and associated threaded pins 214 receive, respectively, the left ends of each of the legs 206. In this respect, the legs 206 include centered tapped holes for mating with the threaded pins 214. The right end 218 of each of the legs 206 is tapered and includes a slot 220 provided on the axially facing end for receiving a screwdriver when coupling and de-coupling the legs from the trunk portion 204. As with the elongated cylindrical mandrel 150 described above, each of the components of the mandrel 200 comprises stainless-steel, or other similar expedient.

A central shaft stub 222 projects to the left from the first adapter disk 202 and is sized to be gripped by the jaws of the chuck 130. As will be more fully described below in the method of use section, the mandrel 200 has several assembled states, some of them including additional adapter disks, all rotatably driven by the chuck 130 and underneath the cutting instrument 114. In this manner, bifurcated grafts, such as the graft shown in FIG. 5, are formed in a series of sequential steps.

Method of Forming Straight Grafts

With reference to FIGS. 3 and 6, the steps in forming straight grafts with the system 100 of the present invention will now be described. First, a length of biocompatible fabric tube is procured. In a preferred embodiment, grafts of the present invention are formed from tubes of polyester terephthalate, commonly known in the industry by its trade name Dacron. A supplier of biocompatible fabric tubes suitable for forming the grafts of the present invention is Prodesco.

The fabric tube 162 is then fitted over the cylindrical mandrel 150 and the assembly is positioned between the chuck 130 and support wheels 136. As will be explained more clearly below with respect to preferred laser parameters, the fabric tube 162 desirably closely fits over the mandrel 150 without any looseness or spaces therebetween.

To rotationally calibrate the fabric tube 162 with respect to the output lens 116, an axial seam or selvage line is oriented to face upward. This can be done manually, or alternatively, the left shaft stub 152 of the mandrel 150 may include some type of registering device limiting the insertion into the jaws of the chuck 130 to only one rotational orientation. In the latter instance, assuming the fabric tube 162 is fitted over the mandrel 150 in a predetermined rotational position with respect to the registering device, the control system 140 may automatically position the selvage line at the upper generatrix of the mandrel/tube assembly. This automated calibration technique removes any guess work of the operator once the mandrel 150 is mounted in the system 100. In other words, the calibration operation takes place off-line when the fabric tube 162 is fitted onto the mandrel 150.

Linear calibration between the cutting instrument 114 and fabric tube 162 is accomplished by making a test cut on a paper model overlying the tube 162. Thus, for example, the control system 140 commands the linear displacement mechanism to position the cutting instrument 114 at the left end of the fabric tube 162 adjacent the chuck 130. The laser 106 generates a beam of light energy which is directed directly downward onto the paper model, while simultaneously the servo motor 128 causes the mandrel 150 to rotate. In this manner, a clean cut around the paper model is made and the paper model is removed. All other linear distances are then measured from this first cut.

As seen in FIG. 3, the notches 60 at the left end of the first straight graft 160 are formed at the time of making the first cut 224 around the tube 162. The notches 60 preferably comprise rounded indentations from the circumferential edge of the graft 160. These rounded notches 60 are formed by synchronizing the linear movement of the cutting instrument 114 with the rotational orientation of the mandrel 150. In a like manner, a plurality of grafts 160 are delineated along the fabric tube 162 by the circumferential cuts interrupted by notches 60. A typical length of fabric tube 162 produces up to eight separate straight grafts of approximately 7.6 cm (3 inches) in length. Of course, as will be appreciated, the need for varying lengths of grafts 160 may necessitate smaller or larger numbers be cut from any one tube 162.

After cutting the first, or calibration, line 224 on the left end of the fabric tube 162, a series of axially spaced circumferential rows 52 of wire-receiving holes 50 are formed in the first graft 160. These holes were described previously with respect to the straight graft 42 of FIG. 3, and serve to receive the support wires 44 as seen in FIG. 2. In this regard, the holes 50 are preferably circular having a diameter equal to or less than the diameter of the support wires. A close fit is provided between the support wires 44 and the holes 50 to prevent leakage through graft 160 upon implantation in a vessel. In one particular embodiment, the support wires 44 have a diameter of 0.3 mm (0.012 inches) and the holes 166 have a diameter of between 0.025–0.279 mm (0.001–0.011 inches), and more preferably between 0.178–0.229 mm (0.007–0.009 inches).

Again, as seen in FIG. 3, each row 52 of wire-receiving holes 50 comprises a plurality of closely spaced pairs 54 of holes, each pair of holes being spaced farther from an adjacent pair of holes been from each other. Each pair 54 of holes 50 thus receives either a crest or a valley of the undulating support wires 44 on the outside of the graft, with the remainder of the support wires being located within the graft. This arrangement was shown in FIG. 2.

Because of the computer control system 140 and synchronized precision movement of the cutting instrument 114 and rotating mandrel 150, the location of each of the holes 50 is very precise. Those of skill in the art in programming will recognize that there are variety of patterns that can be formed on the graft using the tools described herein. The illustrated pattern of axially spaced circumferential rows of holes 166 is preferably formed one row at a time by fixing the location of the cutting instrument 114 and rotating the mandrel 150.

After all of the wire-receiving holes 50 are formed, the first graft 160 is finished by cutting the right end, including the notches 60. The process continues with the system forming first the left end of each graft 160, then the pattern of wire-receiving holes 50, and finally the right end of each graft. In the embodiment shown, the right end of each graft coincides with the left end of the adjacent graft, with the respective notches being cut in opposite directions and at the same location. This of course reduces the amount cutting and associated fabrication time. In an alternative embodiment, a space may be formed between each of the grafts 160. Because of the close fit between the fabric tube 162 and mandrel 150, supplemental restraints holding the tube to the mandrel may not be needed. Of course, various forms of straps or elastomeric rings, for example, may be utilized to secure the fabric tube onto the mandrel.

Method of Forming Bifurcated Grafts

Figure 8:
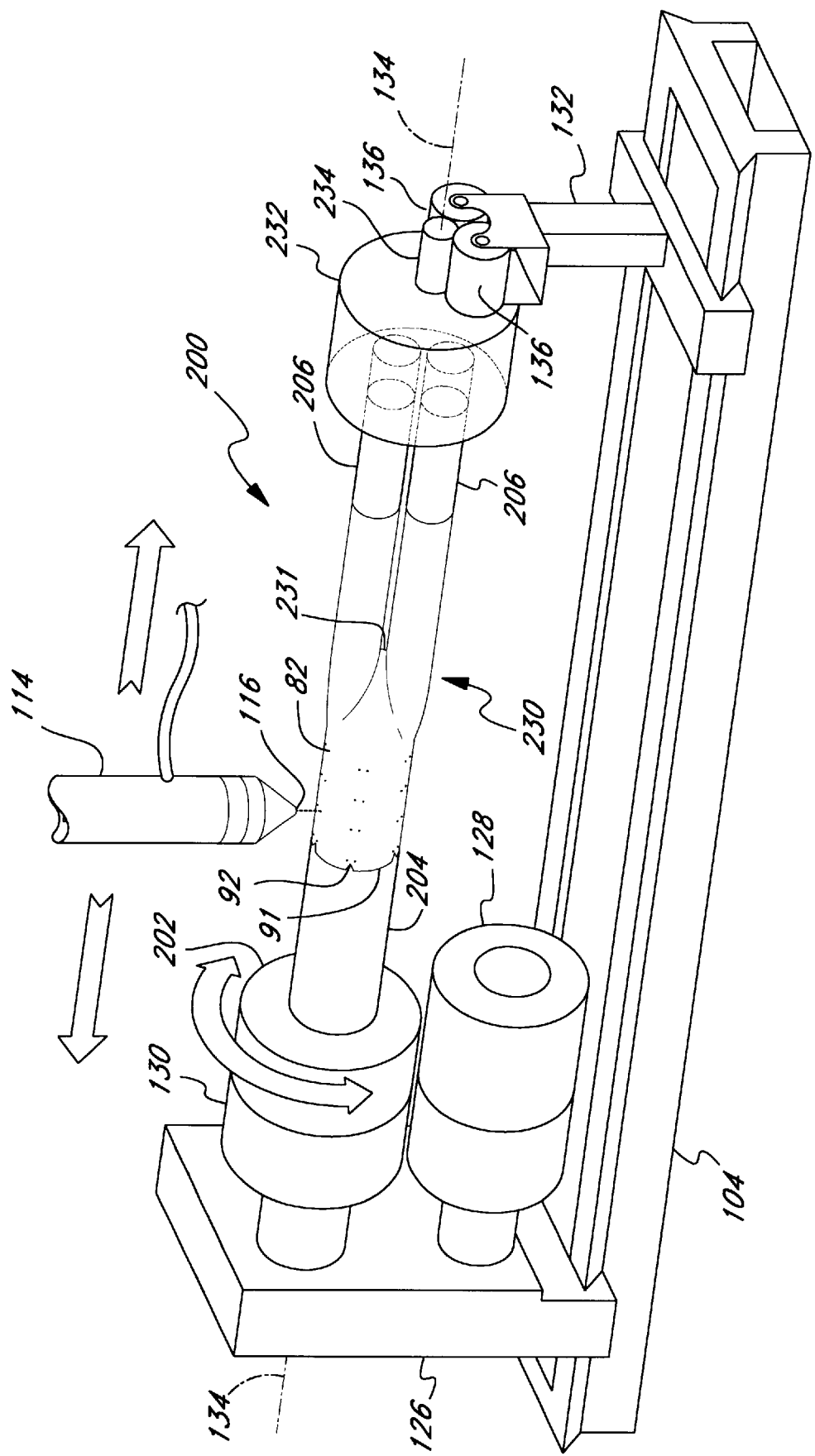
FIG. 8 is a perspective view of a portion of the graft forming system with the mandrel in FIG. 7 assembled and showing a first step in a method of forming a bifurcated graft.
Figure 9:
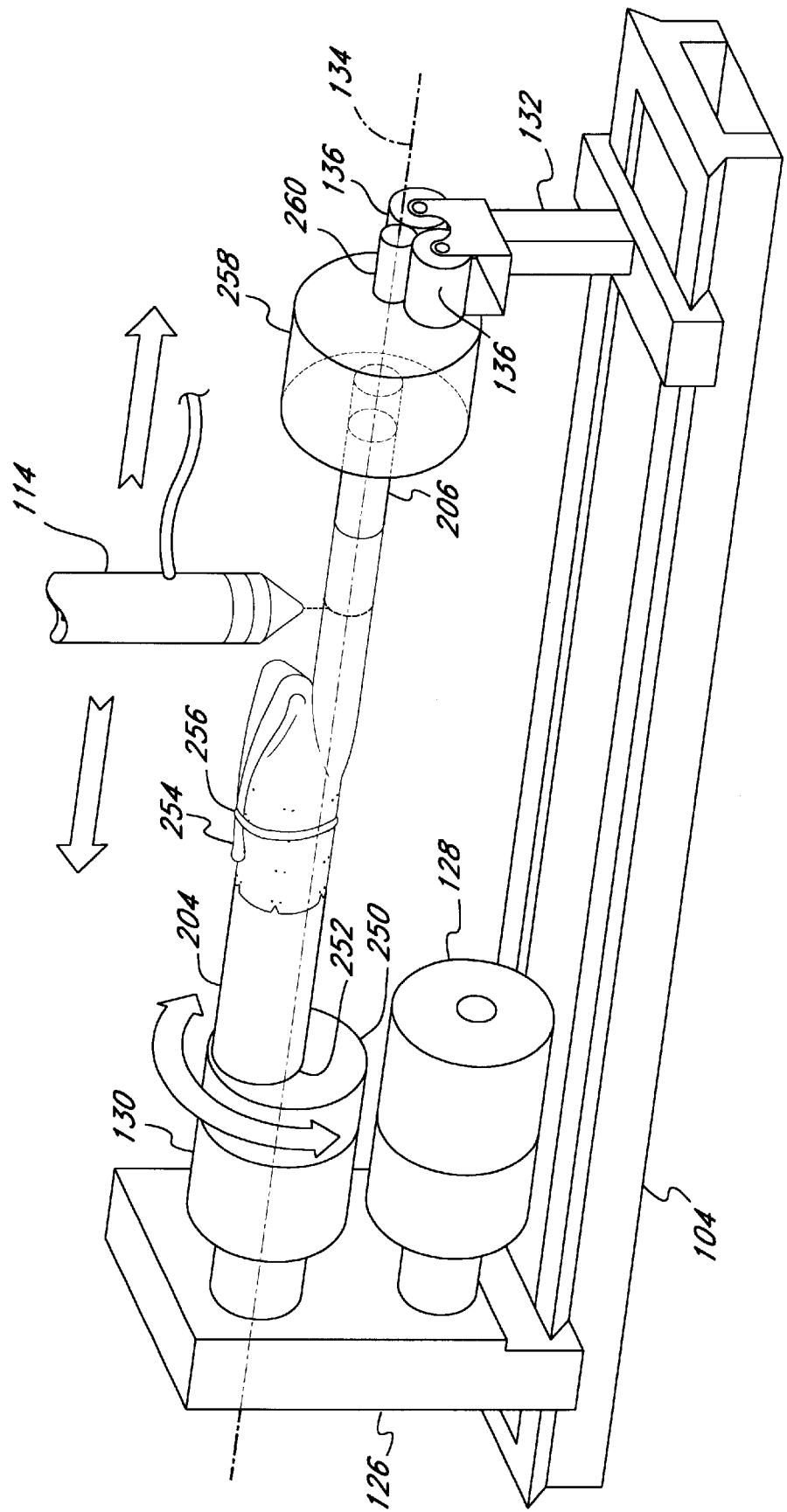
FIG. 9 is a perspective view as in FIG. 8 showing a second step in the method of forming a bifurcated graft.
Figure 10:
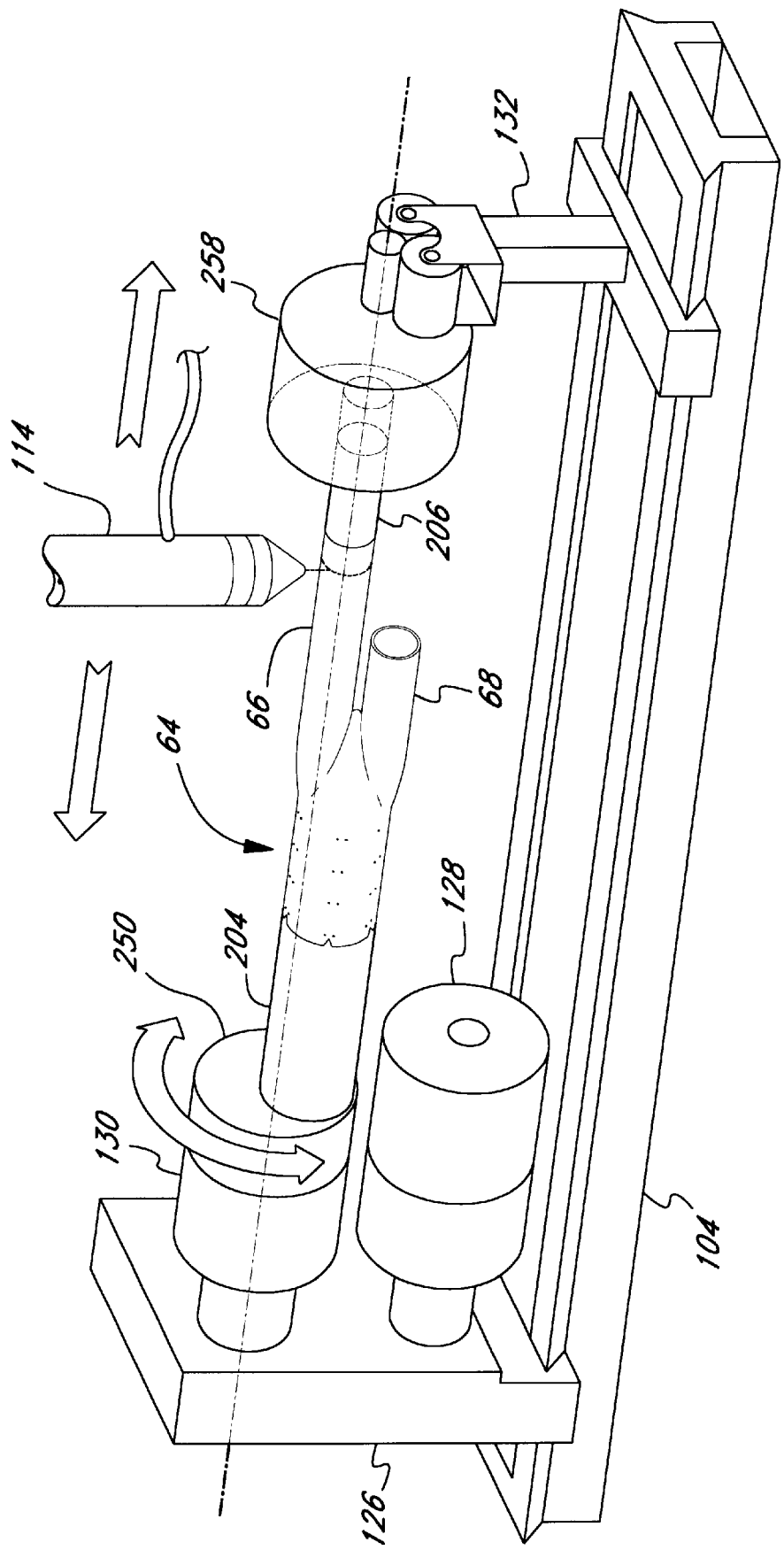
FIG. 10 is a perspective view as in FIG. 8 showing a third step in the method of forming a bifurcated graft.

FIGS. 8–10 illustrates three snapshots or stages of forming the bifurcated graft 72 seen in FIG. 5. Initially, an unfinished bifurcated graft is procured from a source such as Prodesco. In forming the unfinished bifurcated graft, the graft is preferably shrunken onto a forming mandrel having approximately the same shape as the assembled mandrel 200 (seen exploded in FIG. 7). FIG. 8 illustrates an assembled mandrel 200 with the adapter disk 202 being clamped by the jaws of the chuck 130, the left end of the trunk portion 204 being inserted and retained within the cavity 208 (FIG. 7), and the two legs 206 being screwed into the reliefs 212 on the right end of the trunk portion. An unfinished bifurcated graft 230 shown closely fitted over the assembled mandrel 200. Again, the size and shape of the mandrel 200 with respect to the unfinished graft 230 is such that no looseness or spaces exist therebetween.

The unfinished bifurcated graft 230 includes a septum region 231 which contacts the tip 210 (FIG. 7) of the conical end of the trunk portion 204 of the mandrel 200. By sliding the bifurcated graft 230 over the legs 206 and over the trunk portion 204, the septum region 231 eventually contacts and is stopped by the tip 210. In this manner, the bifurcated graft 230 is located with respect to the mandrel 200 as an initial step in registering the graft with respect to the cutting instrument 114. That is, various means will be apparent one of skill the art for calibrating the location of the cutting instrument 114 with respect to the mandrel 200 mounted in the system 100, and the registration of the graft 230 with respect to the mandrel 200 completes the overall calibration.

A leg adapter disk 232 is shown on the right end of the mandrel 200. The adapter disk 232 includes a pair of apertures for receiving the right ends of the legs 206, and a centered shaft stub 234 sized the same as each of the legs. The shaft stub 234 is rotatably supported by the two wheels 136. In this manner, the mandrel 200 in conjunction with the leg adapter disk 232 rotates about the axis 134 and is supported at both axial ends.

The cutting instrument 114 is seen in FIG. 8 forming the mouth 91 of the bifurcated graft 72. After the mouth 91 is formed, the computer control system 140 commands the servo motors and laser 106 to form the plurality of axially spaced circumferential rows of wire-receiving holes 82, and the notches 92. Again, these holes 82 are sized to closely receive the support wires 74 used in the final prosthesis, as seen in FIG. 4. Once the holes 82 are formed, the trunk portion 64 is finished and the legs 66, 68 of the graft are cut to size in the steps seen in FIGS. 9 in 10.

In FIG. 9, the mandrel 200 has been reconfigured by replacing the first adapter disk 202 with a second adapter disk 250. The second adapter disk 250 includes an off-center cavity 252 for receiving the mandrel trunk portion 204. In addition, one of the legs 206 has been removed and the now unsupported leg 254 of the unfinished graft is shown folded back upon the trunk portion of the graft and fastened thereto with a band 256 or other such device. The remaining mandrel leg 206 is received by a centered hole in a second leg adapter disk 258 having a shaft stub 260 rotatably supported by the wheels 136. The remaining mandrel leg 206 is oriented with respect to the second adapter disk 250 to be aligned with the axis 134. In this manner, when the shaft stub of the second adapter desk 250 is captured in the jaws of the chuck 130, the remaining mandrel leg 206 rotates about the axis 134.

The cutting instrument 114 is seen above the mandrel leg 206 cutting the short graft legs 68 to size. Any other notching or hole forming in the short graft leg 68 is accomplished at this time.

In FIG. 10, the mandrel 200 essentially remains in the same configuration as in FIG. 9, but the graft fitted thereon has been removed and re-fitted with the uncut leg positioned over the remaining mandrel leg 206. In this arrangement, the short graft leg 68 extends freely to the right. There is no need to restrain the already cut short graft leg 68 because the cutting instrument 114 only has to cut the longer graft leg 66 to size, and the short leg will not be in the way.

After the longer graft leg 66 is cut, the bifurcated graft is in the configuration seen in FIG. 5. At this point, the assorted support wires and other hardware are added in a separate assembly step to form the prosthesis seen in FIG. 4.

Preferred Cutting Instruments

A variety of different cutting instruments 114 may be utilized in the formation of the grafts in accordance with present invention. A preferred cutting instrument 114 is a laser with an appropriate power and wave length that will allow the removal of the graft material without damage to the mandrel material. In addition the laser must have the ability to modulate the power output. The laser power should be low enough to avoid excessive melting or burning of the material in the graft, while still being strong enough to cut a hole therein and fuse the otherwise frayed ends of fabric material. A particularly useful kind of laser for this invention is a low-power, sealed RF-excited $CO_2$ laser. $CO_2$ lasers are, for the most part, less expensive and more compact than other types of lasers, have the ability to modulate the power output and have a wavelength that is easily absorbed by the graft material. Alternatively, a YAG laser may be suitable although it is somewhat larger and more expensive than a $CO_2$ laser and harder to control the power output.

As mentioned, the holes 50, 82 in the grafts for receiving the wire forms are preferably circular and have a diameter of between 0.178 mm (0.007 inches) and 0.229 mm (0.009 inches). The spot size of the laser beam therefore must be sized to avoid creating larger holes than this preferred range. Laser beams typically have a Gaussian distribution, and thus the spot size must be undersized to accommodate for some widening of the hole because of secondary fringe energy present adjacent the primary beam causing the laser to cut or drill a larger kerf than the spot size. In one the example, therefore, a laser beam as a spot size of about 0.006 inches, and the Gaussian distribution therefore expands that width by about 50% to result in an effective cutting width of 0.009 inches.

A specific example of laser suitable for manufacturing the grafts in accordance with the present invention is a 25 watt $CO_2$ laser available from Synrad of Mulelteo, Wash. Moreover, the power must be attenuated to avoid burning the graft material. For example, the power is preferably set at an output of 7% of the total. $CO_2$ lasers are particularly useful for forming grafts made of synthetic fabrics which efficiently absorb the light energy produced at the infrared wavelengths characteristic of $CO_2$ lasers. In other words, the light energy is absorbed primarily by the graft material, reflected or absorbed by the underlying mandrel.

In this regard, a word should be said about the necessity for a close fit between the graft material and the mandrel. If looseness or spaces exist therebetween, some of the light energy will continue through the hole being formed and will either excessively heat, or be reflected by, the underlying mandrel thus heating the underside of the edges of the hole being formed. This excess heating of the mandrel can be detrimental to the hole forming process. Therefore, it is particular important to size the mandrel so as to form a tight or close fit with the graft material. Furthermore, the mandrels are preferably formed with curved or tapered ends to avoid snagging on the graft material and thus to facilitate assembly thereover and reduce rejects.

Finally, though lasers are particularly useful for forming the grafts as described herein, especially fabric grafts to prevent fraying, the advantages of the graft forming system may also be utilized with other cutting instruments such as a mechanical cutter and the like. In particular, if the graft material does not tend to fray, such as PTFE grafts, then a blade or die stamp may be substituted for the laser such as in the configuration of FIG. 8.

Production Graft Forming

The present invention has so far been described with respect to a single rotating chuck 130 for holding a single cylindrical or bifurcated mandrel. This arrangement is suitable for describing the essential elements of the respective graft forming systems but may be limited in its production capacity. In the alternative, multiple chuck devices may be used for forming a plurality of grafts or performing different steps simultaneously. Such devices may be obtained from Beam Dynamics, of San Carlos, Calif.

In one example of a production device, four parallel chucks in 4 rotary devices are processed in series with only one setup. Four elongated cylindrical mandrels, such as the mandrel 150 shown in FIG. 6, are then fitted with tubes of graft material and installed for rotation by each of the chucks. Each mandrel is processed in series by cutting eight individual grafts from the tubes, after which the mandrels and cut grafts are removed and replaced immediately by new mandrels having uncut tubes thereon. In this manner, the time-consuming step of cleaning and manually fitting each of the mandrels with the tubes of graft material, and removing each of the cut grafts is accomplished off-line, during the cutting process, optimizing the throughput of the system.

A multiple chuck machine is also well-suited for rapidly forming a plurality of the bifurcated grafts 72 seen in FIG. 5. In particular, a four chuck machine can be utilized to process different steps in the sequence shown in FIGS. 8–10. That is, a first pair of chucks may be used to rotate mandrels 200 in the configuration of FIG. 8 while cutting the mouth 91 and notches 92, as well as the pattern of holes 82 in the trunk portion 64. While the first two chucks are being used to perform the more elaborate cutting steps of FIG. 8, the second two chucks may be used to cut the legs to size, as seen in FIGS. 9–10. Those of skilled in the art will recognize that a multiple-chuck machine greatly facilitates the throughput by permitting the time-consuming manual tasks of fitting the grafts over the mandrels and reconfiguring the mandrels to be accomplished off-line.

In a multiple chuck machine, multiple lasers or a single laser supplying light beams to a series of movable reflective mirrors and cutting instruments may be used.

Additionally, the power of the laser may be increased and then "dumped" to result in less power fluctuations. That is, the first embodiment suggested a 25 watt laser at 7% power. Another example is a 50 watt laser from Coherent of Santa Clara, Calif. which is operated at a higher percentage of its maximum power, perhaps 25–50%. The power is then dumped at one of the reflective mirrors which is designed to reflect only a portion of the light and transmit the remainder to a light absorbent black box structure. For example, perhaps 80% of the output beam is dumped, the remaining 20% being used to form the grafts. As a result, any power fluctuations of the laser as it continues to operate and heat up are relatively less harmful to the process. That is, the fluctuations undergo the same relative reduction in power and thus the absolute changes in power are reduced also (to 20% in the exemplary embodiment).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of forming a tubular prosthesis, comprising:
   providing a tube of biocompatible material;
   fitting the tube on a rotatable mandrel;
   directing a laser beam onto the tube of sufficient power to cut through the material without excessive melting or burning of the material;
   forming a graft portion of the prosthesis from the tube;
   forming a plurality of spaced holes around the circumference of the graft;
   removing the graft from the mandrel;
   weaving at least one support wire through the spaced holes and around the circumference of the graft;
   wherein the tube of biocompatible material is a fabric, the plurality of spaced holes comprises a plurality of axially spaced, and closely spaced, circumferential rows of holes;
   wherein the support wires have an undulating shape with crests and valleys, and wherein the wires are passed out through one of each pair of holes and back in through the other of each pair of holes so that only a small portion of each of the wires is exposed to the exterior of the tube, and wherein the holes are undersized with respect to the thickness of the support wires to create an interference fit therebetween.

2. A method of forming a tubular prosthesis, comprising:
   providing a tube of biocompatible material;
   fitting the tube on a rotatable mandrel;
   directing a laser beam onto the tube of sufficient power to cut through the material without excessive melting or burning of the material;
   forming a graft portion of the prosthesis from the tube;
   forming a plurality of spaced holes around the circumference of the graft;
   removing the graft from the mandrel;
   weaving at least one support wire through the spaced holes and around the circumference of the graft;
   wherein the tube of biocompatible material is a fabric, the plurality of spaced holes comprises a plurality of axially spaced, and closely spaced, circumferential rows of holes;
   wherein the support wires have an undulating shape with crests and valleys, and wherein the wires are passed out through one of each pair of holes and back in through the other of each pair of holes so that only a small portion of each of the wires is exposed to the exterior of the tube, and wherein the holes are undersized with respect to the thickness of the support wires to create an interference fit therebetween; and,
   wherein the holes are less than 95% of the thickness of the support wires.

3. A method of forming a tubular prosthesis, comprising:
   providing a tube of biocompatible material;
   fitting the tube on a rotatable mandrel;
   directing a laser beam onto the tube of sufficient power to cut through the material without excessive melting or burning of the material;
   forming a graft portion of the prosthesis from the tube;
   forming a plurality of spaced holes around the circumference of the graft;
   removing the graft from the mandrel;
   weaving at least one support wire through the spaced holes and around the circumference of the graft;
   wherein the tube of biocompatible material is a fabric, the plurality of spaced holes comprises a plurality of axially spaced, and closely spaced, circumferential rows of holes;
   wherein the support wires have an undulating shape with crests and valleys, and wherein the wires are passed out through one of each pair of holes and back in through the other of each pair of holes so that only a small portion of each of the wires is exposed to the exterior of the tube, and wherein the holes are undersized with respect to the thickness of the support wires to create an interference fit therebetween; and,
   wherein the holes are between 8–92% of the thickness of the support wires.

4. A method of forming a tubular prosthesis, comprising:
   providing a tube of biocompatible material;
   fitting the tube on a rotatable mandrel;
   directing a laser beam onto the tube of sufficient power to cut through the material without excessive melting or burning of the material;
   forming a graft portion of the prosthesis from the tube;
   forming a plurality of spaced holes around the circumference of the graft;
   removing the graft from the mandrel;
   weaving at least one support wire through the spaced holes and around the circumference of the graft;
   wherein the tube of biocompatible material is a fabric, the plurality of spaced holes comprises a plurality of axially spaced, and closely spaced, circumferential rows of holes;
   wherein the support wires have an undulating shape with crests and valleys, and wherein the wires are passed out through one of each pair of holes and back in through the other of each pair of holes so that only a small portion of each of the wires is exposed to the exterior of the tube, and wherein the holes are undersized with respect to the thickness of the support wires to create an interference fit therebetween; and, wherein the holes are between the 58–75% of the thickness of the support wires.

5. A method of forming a tubular prosthesis, comprising:

providing a tube of biocompatible material;

fitting the tube on a rotatable mandrel;

directing a laser beam onto the tube of sufficient power to cut through the material without excessive melting or burning of the material;

forming a graft portion of the prosthesis from the tube;

forming a plurality of spaced holes around the circumference of the graft;

removing the graft from the mandrel;

weaving at least one support wire through the spaced holes and around the circumference of the graft;

wherein the tube of biocompatible material is a fabric, the plurality of spaced holes comprises a plurality of axially spaced, and closely spaced, circumferential rows of holes;

wherein the support wires have an undulating shape with crests and valleys, and wherein the wires are passed out through one of each pair of holes and back in through the other of each pair of holes so that only a small portion of each of the wires is exposed to the exterior of the tube, and wherein the holes are undersized with respect to the thickness of the support wires to create an interference fit therebetween; and, wherein the holes are between 8–92% of the thickness of the support wires.

6. A method of forming a tubular prosthesis, comprising:

providing a tube of biocompatible material;

fitting the tube on a rotatable mandrel;

directing a laser beam onto the tube of sufficient power to cut through the material without excessive melting or burning of the material;

forming a graft portion of the prosthesis from the tube;

forming a plurality of spaced holes around the circumference of the graft;

removing the graft from the mandrel;

weaving at least one support wire through the spaced holes and around the circumference of the graft;

wherein the tube of biocompatible material is a fabric, the plurality of spaced holes comprises a plurality of axially spaced, and closely spaced, circumferential rows of holes;

wherein the support wires have an undulating shape with crests and valleys, and wherein the wires are passed out through one of each pair of holes and back in through the other of each pair of holes so that only a small portion of each of the wires is exposed to the exterior of the tube, and wherein the holes are undersized with respect to the thickness of the support wires to create an interference fit therebetween; and, wherein the laser is at least one of a low powered, sealed, RF-excited laser and a $CO_2$ laser.

7. A method of forming a tubular prosthesis, comprising:

providing a tube of biocompatible material;

fitting the tube on a rotatable mandrel;

directing a laser beam onto the tube of sufficient power to cut through the material without excessive melting or burning of the material;

forming a graft portion of the prosthesis from the tube;

forming a plurality of spaced holes around the circumference of the graft;

removing the graft from the mandrel;

weaving at least one support wire through the spaced holes and around the circumference of the graft;

wherein the tube of biocompatible material is a fabric, the plurality of spaced holes comprises a plurality of axially spaced, and closely spaced, circumferential rows of holes;

wherein the support wires have an undulating shape with crests and valleys, and wherein the wires are passed out through one of each pair of holes and back in through the other of each pair of holes so that only a small portion of each of the wires is exposed to the exterior of the tube, and wherein the holes are undersized with respect to the thickness of the support wires to create an interference fit therebetween;

wherein the mandrel is sized such that the tube fits closely thereon with no gaps or looseness therebetween;

wherein the mandrel is a cylinder and the tube and resulting graft are also straight cylinders;

wherein the mandrel comprises a trunk portion and pair of connected leg portions, and the tube is bifurcated;

the steps further comprising at least one of;

mounting the trunk portion to rotate concentrically about an axis;

forming the holes and then reconfiguring the mandrel so that the trunk portion is off-center with respect to the axis and one of the leg portions rotates concentrically about the axis, a first leg of the tube being fitted on the concentrically rotatable leg portion; and cutting the tube on the concentric leg portion to forming a first leg of the graft, and reconfiguring the mandrel so that the trunk portion is off-center with respect to the axis and the second leg of the tube is fitted on the leg portion rotatable concentrically about the axis; and cutting the tube on the concentric leg portion to form the second leg of the graft.

* * * * *